(12) United States Patent
Williams

(10) Patent No.: US 10,842,518 B2
(45) Date of Patent: Nov. 24, 2020

(54) SURGICAL GRASPING INSTRUMENT

(71) Applicant: Covidien LP, Mansfield, MA (US)

(72) Inventor: Justin Williams, Southbury, CT (US)

(73) Assignee: Covidien LP, Mansfield, MA (US)

( * ) Notice: Subject to any disclaimer, the term of this patent is extended or adjusted under 35 U.S.C. 154(b) by 241 days.

(21) Appl. No.: 16/120,509

(22) Filed: Sep. 4, 2018

(65) Prior Publication Data

US 2019/0133629 A1    May 9, 2019

Related U.S. Application Data

(60) Provisional application No. 62/581,063, filed on Nov. 3, 2017.

(51) Int. Cl.
*A61B 17/29* (2006.01)
*A61B 17/12* (2006.01)
(Continued)

(52) U.S. Cl.
CPC .............. *A61B 17/29* (2013.01); *A61B 17/12* (2013.01); *A61B 17/122* (2013.01); *A61B 5/021* (2013.01); *A61B 5/026* (2013.01); *A61B 5/6847* (2013.01); *A61B 5/6879* (2013.01); *A61B 2017/00544* (2013.01); *A61B 2017/00557* (2013.01); *A61B 2017/00907* (2013.01);
(Continued)

(58) Field of Classification Search
CPC ....... A61B 17/29; A61B 17/12; A61B 17/122; A61B 2017/00544; A61B 2017/00557; A61B 2017/00907; A61B 2017/2825; A61B 2017/2932; A61B 2017/2944; A61B 2017/2934; A61B 2017/2933
See application file for complete search history.

(56) References Cited

U.S. PATENT DOCUMENTS

| 4,848,338 A | * | 7/1989 | De Satnick | A61B 17/29 606/1 |
| 5,156,161 A | | 10/1992 | Lollar | |
| 5,397,046 A | * | 3/1995 | Savage | A61B 17/07207 227/175.3 |
| 5,478,003 A | * | 12/1995 | Green | A61B 17/07207 227/176.1 |

(Continued)

OTHER PUBLICATIONS

Written Opinion and International Search Report dated Feb. 11, 2019, issued in PCT/US2018/057431.

*Primary Examiner* — Katrina M Stransky
(74) *Attorney, Agent, or Firm* — Carter, DeLuca & Farrell LLP

(57) ABSTRACT

A grasping instrument for clamping tissue includes an outer tube, first and second jaw members supported by the outer tube, a carriage mounted within the outer tube and configured for longitudinal movement between an initial proximal position and an advanced distal position to cause corresponding movement of the first and second jaw members between an approximated condition and an open condition, a piston operatively coupled to the carriage, an inflatable membrane disposed within the piston and being selectively inflatable to a predefined internal pressure to cause corresponding distal longitudinal movement of the piston a predetermined distance and to cause proximal longitudinal movement of the carriage to apply a clamping force to the tissue disposed within the first and second jaw members and an indicator bar having visual indicators corresponding to various degrees of thickness of the tissue disposed within the first and second jaw members.

16 Claims, 12 Drawing Sheets

(51) Int. Cl.
*A61B 17/122* (2006.01)
*A61B 17/00* (2006.01)
*A61B 17/28* (2006.01)
A61B 90/00 (2016.01)
A61B 5/026 (2006.01)
A61B 5/021 (2006.01)
A61B 5/00 (2006.01)

(52) U.S. Cl.
CPC .......... *A61B 2017/2825* (2013.01); *A61B 2017/2932* (2013.01); *A61B 2017/2936* (2013.01); *A61B 2017/2944* (2013.01); *A61B 2090/032* (2016.02); *A61B 2090/061* (2016.02); *A61B 2090/063* (2016.02); *A61B 2090/0811* (2016.02)

(56) References Cited

U.S. PATENT DOCUMENTS

| | | | |
|---|---|---|---|
| 5,485,887 A * | 1/1996 | Mandanis | A61B 17/92 173/135 |
| 5,575,799 A * | 11/1996 | Bolanos | A61B 17/0684 227/175.1 |
| 5,618,307 A * | 4/1997 | Donlon | A61B 17/00234 604/158 |
| 2009/0171371 A1 | 7/2009 | Nixon et al. | |
| 2012/0104072 A1 | 5/2012 | Vidal et al. | |
| 2014/0276232 A1 | 9/2014 | Ruff | |
| 2016/0256188 A1 | 9/2016 | Marczyk et al. | |
| 2018/0028183 A1* | 2/2018 | Fakhouri | A61B 17/07207 |
| 2018/0042613 A1* | 2/2018 | Gerosolimo | A61B 17/122 |

\* cited by examiner

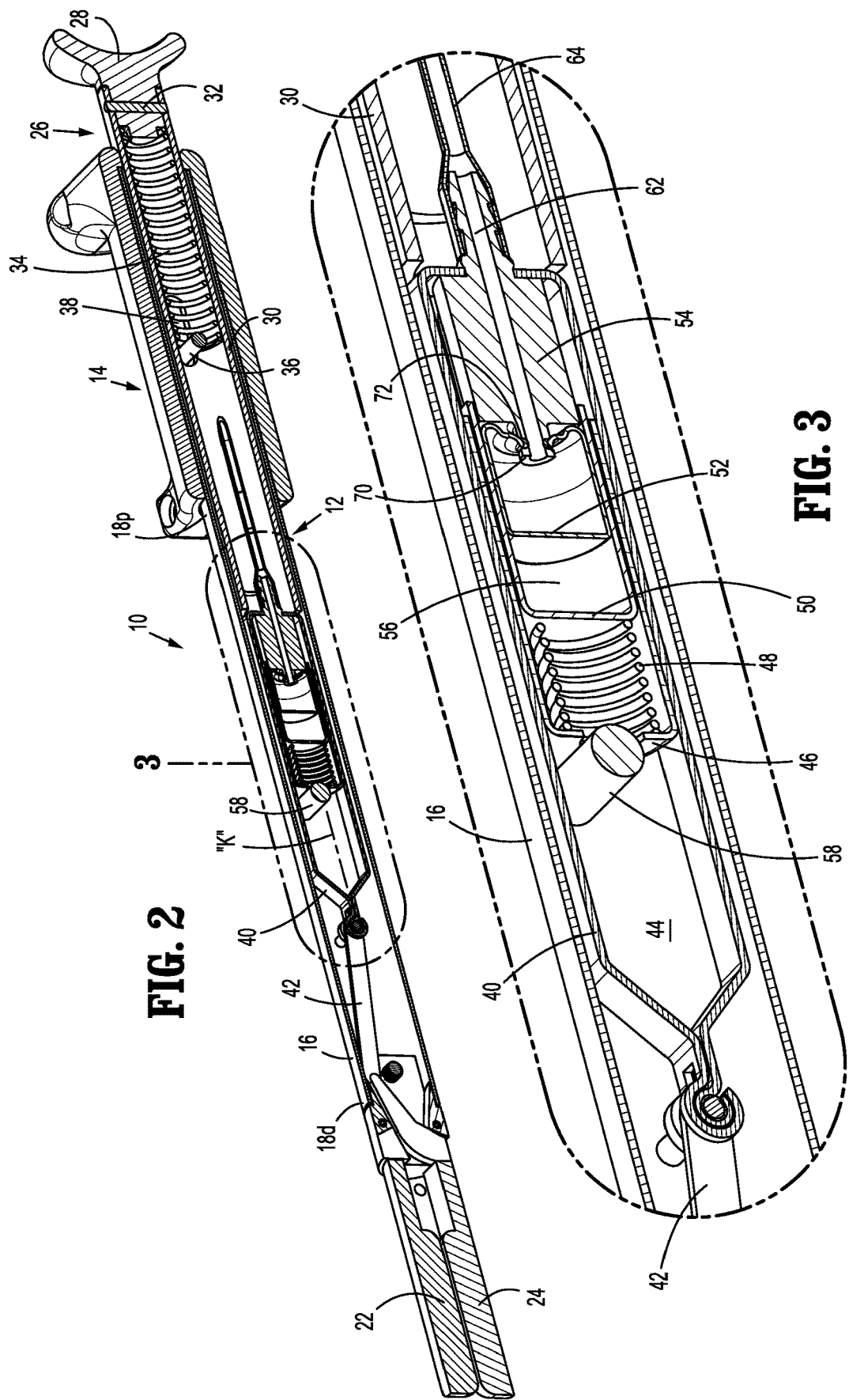

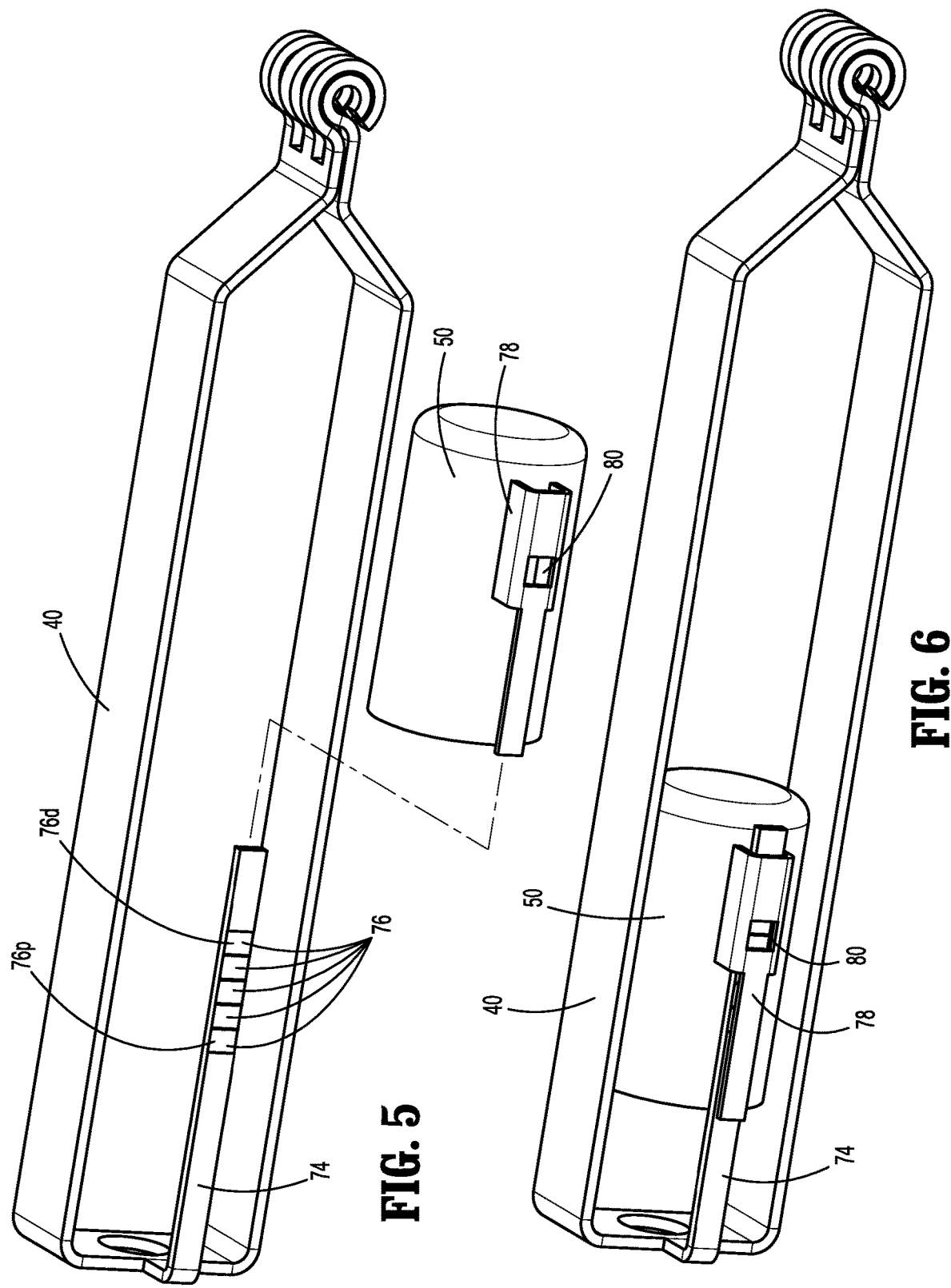

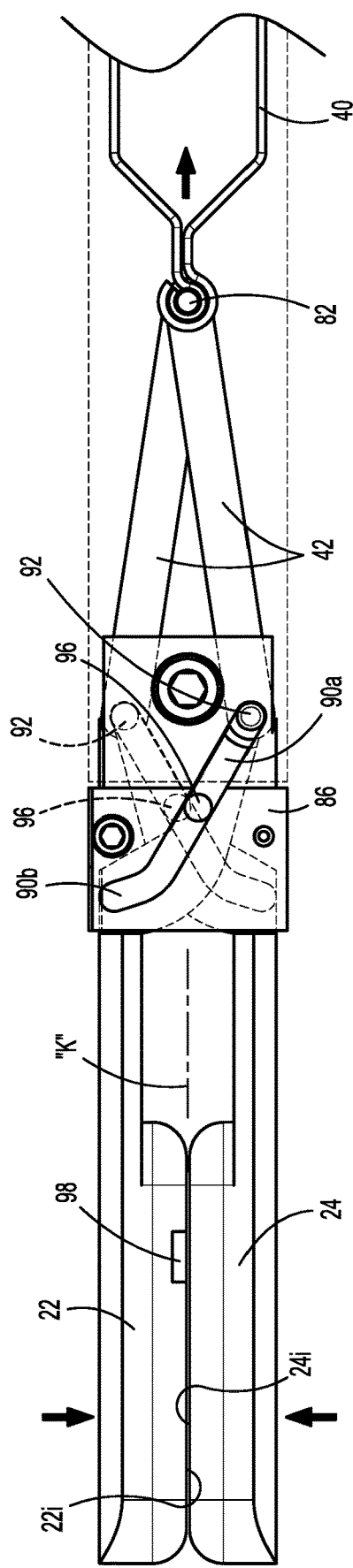
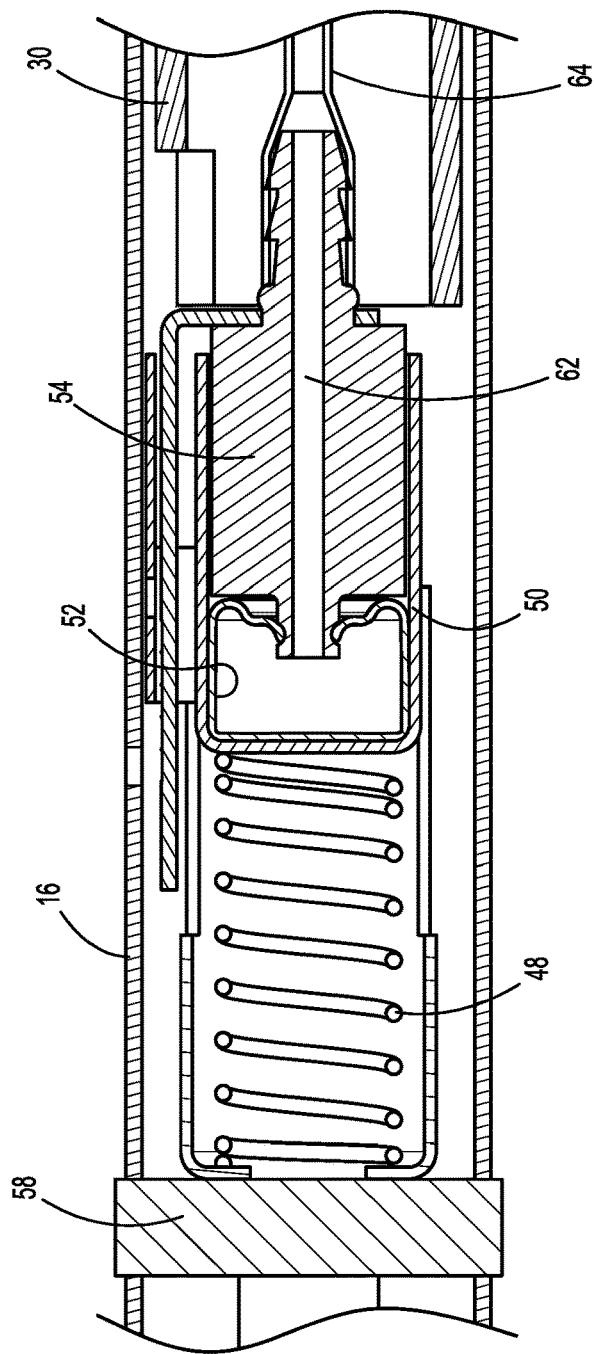
FIG. 7
FIG. 8

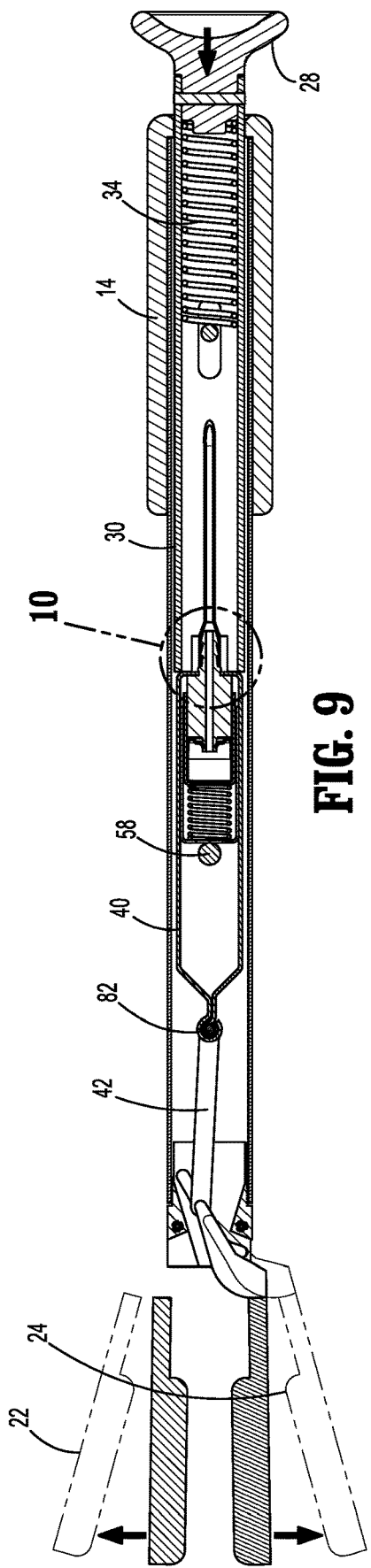
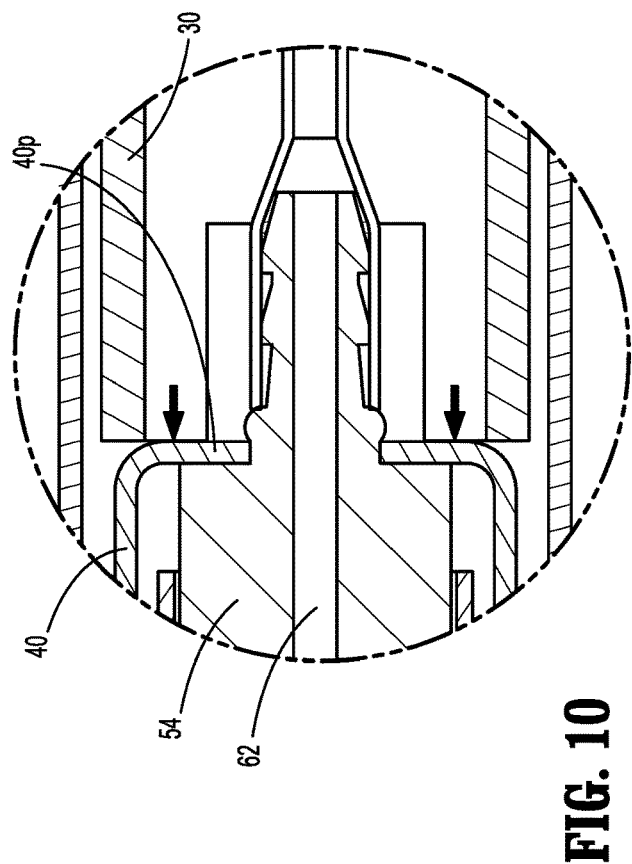
FIG. 9
FIG. 10

SURGICAL GRASPING INSTRUMENT

CROSS-REFERENCE TO RELATED APPLICATION

This application claims the benefit of and priority to U.S. Provisional Patent Application No. 62/581,063 filed Nov. 3, 2017, the entire disclosure of which is incorporated by reference herein.

BACKGROUND

1. Technical Field

The present disclosure relates to a surgical grasping instrument and, more particularly, relates to a grasping instrument having a parallel jaw closure capable of accurately determining the thickness of tissue clamped between the jaws and/or to clamp the tissue uniformly to occlude blood flow.

2. Background of Related Art

Surgical grasping instruments for grasping and clamping tissue are well known in the art. Typically, grasping instruments include a pair of jaws that are movable in relation to each other to clamp tissue positioned between the jaws. In some instruments, the jaws are coupled to each other and are pivotal from an open position to a clamped position. However, during movement of the jaws from the open position to the clamped position, the clamped tissue tends to extrude from between the jaws, which results in uneven pressure distribution on the tissue. This uneven pressure distribution may result in an ineffective occlusion of the tissue, particularly, if the tissue is a blood vessel and the intent is to occlude blood flow through the vessel. In addition, due in at least in part to the uneven pressure distribution, known grasping instruments are deficient in adequately measuring the thickness of tissue clamped between the jaws.

SUMMARY

Accordingly, the present disclosure is directed to a grasping instrument for clamping tissue which obviates the deficiencies of conventional grasping instruments. In accordance with one exemplary embodiment, a surgical grasping instrument includes an outer tube defining a longitudinal axis and having proximal and distal ends, first and second jaw members supported adjacent the distal end of the outer tube, and configured for movement between an open condition to receive tissue therebetween and an approximated condition to engage the tissue, a carriage mounted within the outer tube and operatively coupled to the first and second jaw members, and configured for longitudinal movement between an initial proximal position and an advanced distal position to cause corresponding movement of the first and second jaw members between the approximated condition and the open condition, a piston operatively coupled to the carriage, an inflatable membrane disposed within the piston and being selectively inflatable to a predefined internal pressure to cause corresponding distal longitudinal movement of the piston a predetermined distance and to cause proximal longitudinal movement of the carriage to apply a clamping force to the tissue disposed within the first and second jaw members, and an indicator bar coupled to the carriage and having visual indicators corresponding to various degrees of thickness of the tissue disposed within the first and second jaw members when subjected to the clamping force of the first and second jaw members.

In embodiments, the first and second jaw members define internal jaw surfaces which are in general parallel relation during movement toward the approximated condition.

In some embodiments, a drive member is operatively coupled to the carriage and engageable with the inflatable membrane. The drive member is configured for proximal longitudinal movement upon inflation of the inflatable membrane to the predefined internal pressure to cause longitudinal movement of the carriage toward the initial proximal position. In certain embodiments, a spring is disposed adjacent the piston. In embodiments, the spring includes a spring constant configured to limit distal longitudinal movement of the piston for the predetermined distance upon inflation of the inflatable membrane to the predefined internal pressure.

In some embodiments, the outer tube includes a viewing window which permits viewing of one of the visual indicators of the indicator bar when the tissue is subjected to the clamping force. The one of the visual indicators corresponds to a specific degree of thickness of the tissue subjected to the clamping force.

In certain embodiments, the piston includes an indicator mount for at least partial reception of the indicator bar. The indicator mount includes a viewing window positioned to be in alignment with the viewing window of the outer tube upon movement of the piston the predetermined distance to permit viewing of the one of the visual indicators of the indicator bar. In embodiments, the viewing window of the outer tube and the viewing window of the indicator mount are longitudinally displaced when the tissue is subjected to a force greater than the clamping force whereby the visual indicators are not viewable through the viewing windows of the outer tube and the indicator mount.

In some embodiments, the visual indicators of the indicator bar are arranged to correspond to different degrees of thickness of the tissue subjected to the clamping force. The visual indicators may increase in value from distal to proximal along the indicator bar. In certain embodiments, the visual indicators of the indicator bar include different color markings with each color marking corresponding to a selected degree of the thickness of the tissue subjected to the clamping force.

In embodiments, an internal pusher is at least partially disposed within the outer tube. The internal pusher is configured for distal longitudinal movement to engage the carriage and move the carriage to the distal advanced position and the first and second jaw members to the open condition. In some embodiments, the internal pusher is normally biased toward the proximal direction.

In certain embodiments, the drive member defines a flow passage in fluid communication with an internal volume of the inflatable membrane to permit passage of fluids to control inflation of the inflatable membrane.

In embodiments, an internal spring housing is secured within the outer tube, and at least partially accommodates the spring, the piston and the inflatable membrane.

In accordance with another exemplary embodiment, a surgical grasping instrument for clamping tissue includes an outer tube defining a longitudinal axis and having proximal and distal ends, first and second jaw members supported adjacent the distal end of the outer tube, and configured for movement between an open condition to receive tissue therebetween and an approximated condition to engage the tissue whereby internal jaw surfaces of the first and second jaw members are in general parallel relation upon movement toward the approximated condition, a carriage mounted within the outer tube and operatively coupled to the first and second jaw members, and configured for longitudinal movement between an initial proximal position and an advanced distal position to cause corresponding movement of the first and second jaw members between the approximated condition and the open condition, a drive member coupled to the carriage, a piston at least partially accommodating the drive member, an inflatable membrane disposed within the piston adjacent the drive member and being selectively inflatable to a predefined internal pressure to cause corresponding distal longitudinal movement of the piston a predetermined distance and to cause proximal longitudinal movement of the drive member and the carriage to apply a clamping force to the tissue disposed within the first and second jaw members, an indicator bar coupled to the carriage and having visual indicators corresponding to various degrees of thickness of the tissue disposed within the first and second jaw members when subjected to the clamping force of the first and second jaw members, and an internal pusher at least partially disposed within the outer tube, and configured for distal longitudinal movement to engage the carriage and move the carriage to the distal advanced position and the first and second jaw members to the open condition. In embodiments, the visual indicators of the indicator bar include longitudinal markings with respective markings corresponding to the thickness of the tissue subjected to the clamping force.

The grasping instrument of the present disclosure provides for parallel closure of its jaw members to ensure pressure is distributed uniformly to the tissue. This ensures effective closure of the tissue, blood vessel and occlusion of the blood flow therethrough. The grasping instrument also incorporates a tissue measuring mechanism, operating in conjunction with the parallel jaw closure, which provides a precise measurement of tissue secured between the first and second jaw members. This may facilitate performance of a subsequent surgical procedure on the tissue including, e.g., stapling operations where the proper size staple may be identified based on measurement data provided by the instrument.

Other features of the present disclosure will be appreciated from the following description.

BRIEF DESCRIPTION OF THE DRAWINGS

Various aspects and features of the present disclosure are described herein below with reference to the drawings wherein like numerals designate identical or corresponding elements in each of the several views:

FIG. 2 is a perspective view in cross-section of the grasping instrument taken along the lines 2-2 of FIG. 1;

FIG. 3 is an enlarged view of the area of detail identified in FIG. 2;

FIG. 5 is a perspective view of the carriage and the piston with the piston separated from the carriage;

FIG. 6 is a perspective view of the carriage and the piston with the piston mounted to the carriage;

FIG. 7 is an enlarged plan view of the first and second jaw members in an approximated condition;

FIG. 8 is a cross-sectional view of components of the tissue measuring mechanism of the grasping instrument with the first and second jaw members in the approximated condition;

FIG. 9 is a side cross-sectional view of the grasping instrument illustrating the inner member advanced to move the first and second jaw members to an open condition;

FIG. 10 is an enlarged view of the area of detail identified in FIG. 9;

DETAILED DESCRIPTION

Figure 1:
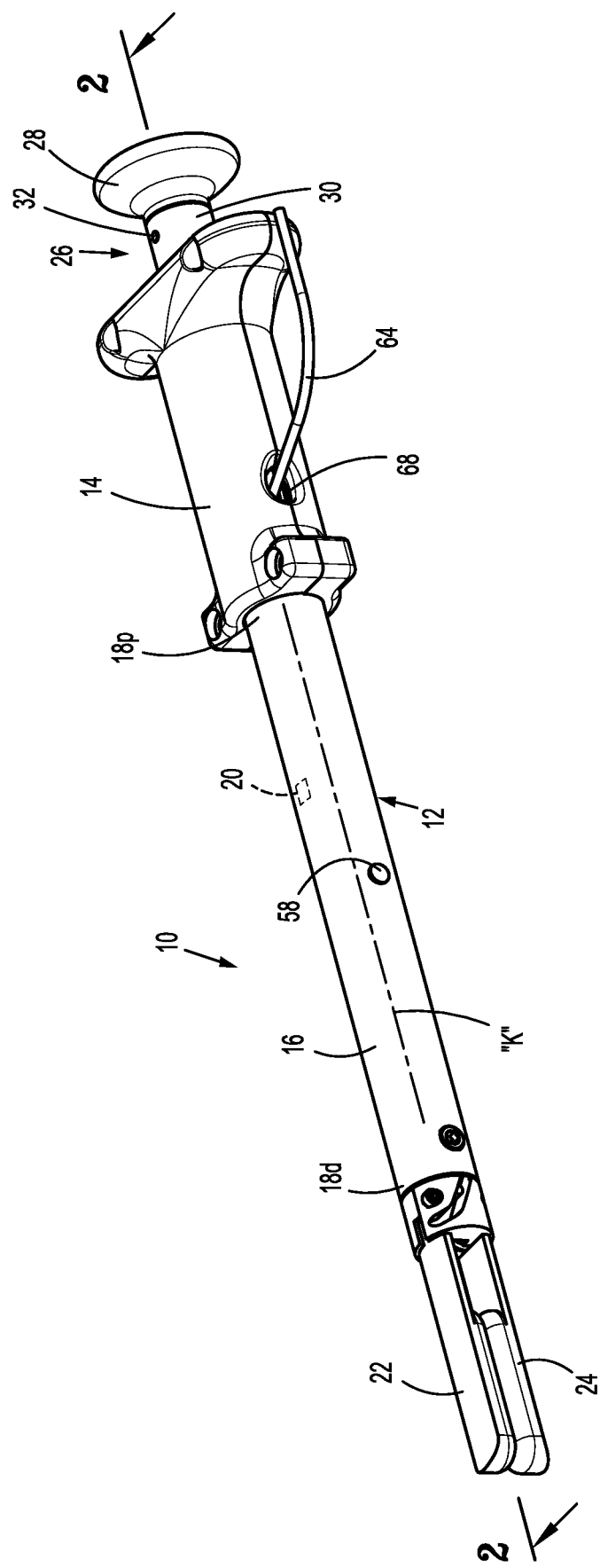
FIG. 1 is a perspective view of the surgical grasping instrument of the present disclosure.

Embodiments of the presently disclosed surgical grasping instrument are described in detail with reference to the drawings, in which like reference numerals designate identical or corresponding elements in each of the several views. As used herein the term "distal" refers to that portion of the surgical grasping instrument, or component thereof, farther from the clinician, while the term "proximal" refers to that portion of the surgical grasping instrument, or component thereof, closer to the clinician.

In general, the present disclosure is directed to a surgical grasping instrument having a parallel jaw closure which uniformly compresses tissue disposed between the jaw members. This uniform compression of tissue facilitates occlusion of, e.g., a blood vessel, to stop blood flow. The surgical instrument further includes a measuring mechanism capable of accurately determining the thickness of tissue grasped between the jaw members of the instrument. The thickness of the tissue calculated by the measuring mechanism may provide information for a subsequent surgical procedure. For example, the measuring mechanism may assist the clinician in determining the staple size or type required in a stapling procedure. The calculated thickness also may provide information related to the health of the tissue.

The measuring mechanism generally includes a piston, an inflatable membrane adapted to be selectively inflated to translate the piston a predetermined distance and to impart motion to a carriage to cause jaw members to clamp tissue therebetween, and an indicator bar associated with the carriage and having visual indicators corresponding to the thickness of the tissue clamped between the jaw members. The jaw members define internal jaw surfaces which assume a general parallel relation upon movement to an approximated condition to evenly compress the tissue to ensure an accurate measurement of the tissue thickness and/or to occlude blood flow through the tissue.

Referring now to the drawings where like reference numerals indicate similar components throughout the several views, FIGS. 1-4 illustrate a surgical grasping instrument 10 of the present disclosure. The surgical grasping instrument 10 includes an outer member 12 having an outer handle 14 and an elongate outer tube 16 extending from the outer handle 14. The outer handle 14 may include handle half sections 14a, 14b (FIG. 4) coupled to each other through conventional methodologies including screws, fasteners or the like. The outer handle 14 is contoured for manual engagement by the clinician. The outer tube 16 has proximal and distal ends 18p, 18d and defines a longitudinal axis "k". The outer tube 16 further includes a viewing window 20 (shown in phantom in FIG. 1) which extends completely through the opposed wall section of the outer tube 16. Supported at the distal end 18d of the outer tube 16 are first and second jaw members 22, 24. The first and second jaw members 22, 24 are configured to move between the approximated condition depicted in FIG. 1 and an open condition.

The grasping instrument 10 further includes an inner pusher 26 at least partially disposed within the outer member 12. The inner pusher 26 includes a manually engageable knob 28 and a pusher tube 30 which terminates about midway within the outer tube 16. The manually engageable knob 28 is secured to the pusher tube 30 via pin 32. A pusher spring 34 normally biases the manually engageable knob 28, and thus, the pusher tube 30, in the proximal direction. In particular, the pusher spring 34 engages, at one end, a spring pin 36 which is fixedly secured to the outer tube 16 and, at its other end, the manually engageable knob 28. The pusher tube 30 defines an elongated slot 38 in its outer wall which accommodates the spring pin 36. The elongated slot 38 permits the pusher tube 30 to move relative to the outer tube 16 through traversing movement of the spring pin 36 within the elongated slot 38.

Disposed within the outer tube 16 are a carriage 40 and a pair of links 42 which are coupled to the carriage 40. The carriage 40 defines an internal enclosure 44 which accommodates components of the tissue measuring mechanism. The links 42 extend to, and are respectively operatively coupled with, the first and second jaw members 22, 24. Movement of the carriage 40 and the links 42 in a proximal direction will cause the first and second jaw members 22, 24 to transition toward the approximated condition while movement of these components in the distal direction will cause the first and second jaw members 22, 24 to transition toward the open condition.

Figure 4:
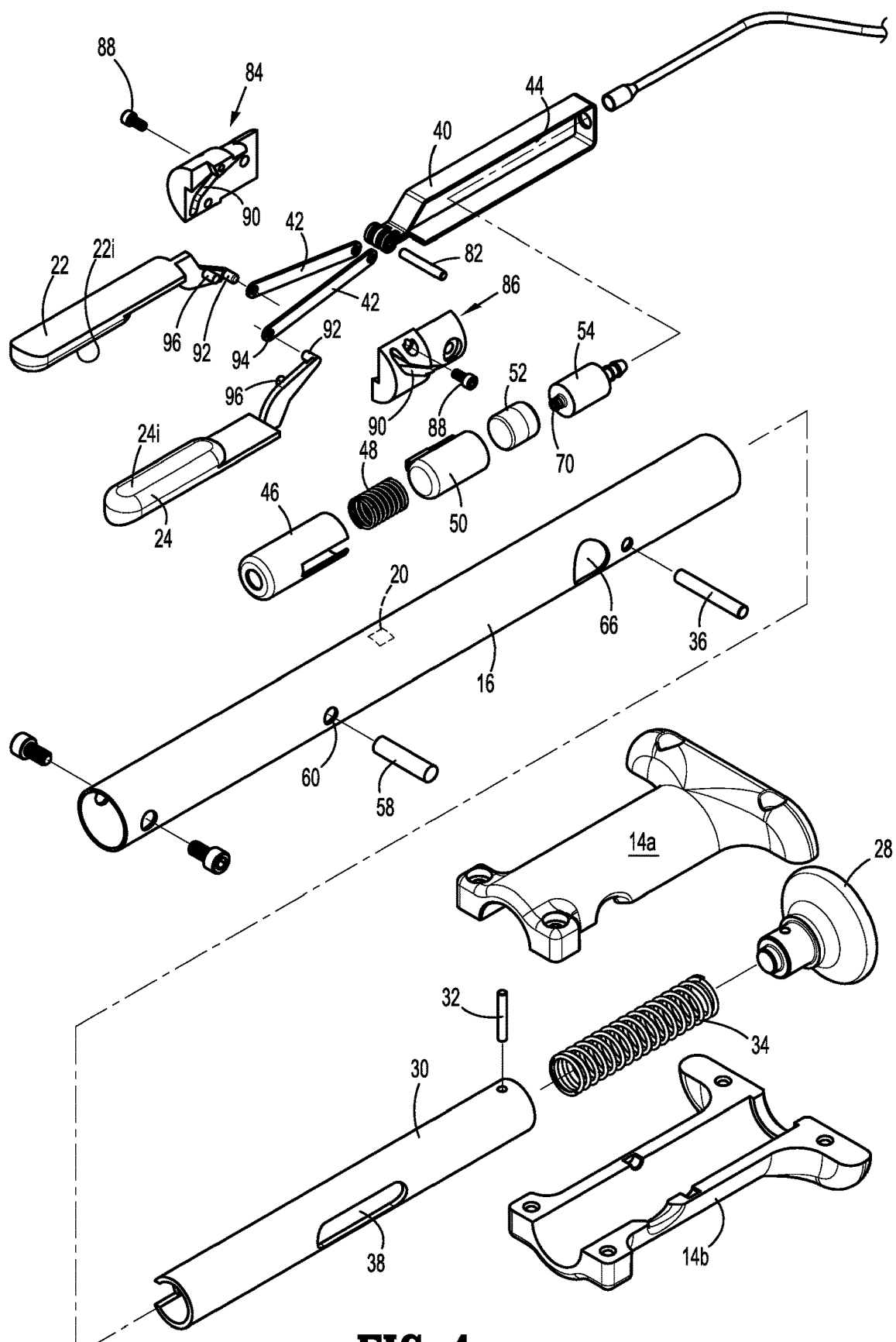
FIG. 4 is an exploded perspective view of the grasping instrument.

With continued reference to FIGS. 2-4, the grasping instrument 10 further includes a spring housing 46, a spring 48 at least partially disposed within the spring housing 46, a piston 50 adjacent the spring 48, an inflatable membrane 52 and a drive member 54. The piston 50 defines an internal chamber 56 for at least partially accommodating the inflatable membrane 52 and the drive member 54. The spring housing 46 is fixed from longitudinal movement by a housing pin 58 extending through corresponding apertures 60 (FIG. 4) of the outer tube 16. The spring 48 engages the piston 50 to normally bias the piston 50 in a proximal direction.

The inflatable membrane 52 is selectively expandable upon introduction of fluids therein. In embodiments, the drive member 54 defines an internal flow passage 62 in fluid communication with an internal volume of the inflatable membrane 52. The flow passage 62 is, in turn, in fluid communication with a fluid conduit 64 coupled to the drive member 54 and extending through respective aligned openings 66, 68 (FIGS. 1 and 4) in the outer tube 16 and the outer handle 14 of the outer member 12. In the alternative, the internal volume of the inflatable membrane 52 may be directly coupled to a fluid conduit. The drive member 54 is coupled to the inflatable membrane 52 whereby inflation of the inflatable membrane 52 causes corresponding proximal longitudinal movement of the drive member 54. Any methodologies for coupling the drive member 54 and the inflatable membrane 52 are envisioned. In an embodiment, the drive member 54 includes a fluid port 70 which extends within an opening 72 in the inflatable membrane 52 in sealed relation therewith.

As best depicted in FIG. 3, the carriage 40 is secured at its proximal end to the drive member 54 such that longitudinal movement of the drive member 54 causes corresponding longitudinal movement of the carriage 40 to transition the first and second jaw members 22, 24 between the approximated and open conditions. Any methodologies to couple the carriage 40 to the drive member 54 are envisioned including cements, adhesives, spot welding or the like.

Referring now to FIGS. 5-6, further details of the carriage 40 and the piston 50 will be discussed. In FIGS. 5-6, only the carriage 40 and the piston 50 are depicted for clarity purposes. The carriage 40 includes an elongated indicator bar 74 extending from its proximal end in general parallel relation with the longitudinal axis "k" of the outer tube 16. The indicator bar 74 includes visual indicators 76 on its outer surface, which may include markings, text, numbers, color codes or the like. In embodiments, the visual indicators 76 include color markings which assist the clinician in visually determining the thickness of the tissue compressed between the first and second jaw members 22, 24. Specifically, each color marking may be a different color and correspond to a thickness of the tissue subjected to the clamping force between the first and second jaw members 22, 24. Alternatively, or additionally, each color marking may include numerical values representative of the thickness of the tissue. The visual indicators 76 increase in value from distal to proximal whereby the distal most indicator 76d corresponds to a relatively thin tissue secured between the first and second jaw members 22, 24 and the proximal most indicator 76p corresponds to relatively thick tissue secured between the first and second jaw members 22, 24. The piston 50 includes an external bar mount 78 which at least partially receives the indicator bar 74 of the carriage 40, and is configured to permit traversing longitudinal movement of the indicator bar 74 therewithin. The bar mount 78 defines a viewing window 80 allowing visualization of individual visual indicators 76 of the indicator bar 74 when aligned with the viewing window 20 of the outer tube 16.

Referring now to FIG. 7, in conjunction with FIG. 4, the links 42 are coupled to the carriage 40 via pin member 82, and are capable of pivoting relative to the pin member 82 during longitudinal movement of the carriage 40. The links 42 are also coupled to first and second jaw mounts 84, 86 which are secured to the outer tube 16 via screws or fasteners 88. Each of the first and second jaw mounts 84, 86 includes a cam groove or slot 90 extending completely through its wall and consisting of a proximal first slot portion 90a arranged at a first oblique angle with respect to the longitudinal axis "k" and a distal second slot portion 90b arranged at a second oblique angle with respect to the longitudinal axis "k". The second oblique angle is greater than the first oblique angle. The cam slot 90 of the first jaw mount 84 is the reverse mirror image of the cam slot 90 of the second jaw mount 86. Each of the first and second jaw members 22, 24 includes a pin mount 92 which couples with apertures 94 of the links 42, and a cam pin 96. The pin mounts 92 and the cam pins 96 traverse the cam slots 90 during longitudinal movement of the carriage 40 and the links 42 to move the first and second jaw members 22, 24 between the approximated and open conditions. The first oblique angles are selected such that, during movement of the pin mounts 92 and the cam pins 96 through the first slot portions 90a, the first and second jaw members 22, 24 move in general parallel relation with respect to each other and the longitudinal axis "k", i.e., the inner jaw surfaces 22i, 24i of the first and second jaw members 22, 24 remain parallel to each other. The first oblique angle may range between 30° and 60° relative to the longitudinal axis "k". Once the cam pins 96 enter the second slot portions 90b, the first and second jaw members 22, 24 open rapidly to an open condition assuming an oblique relationship positioned to receive tissue therebetween. The second oblique angles may range from 60° to 80° relative to the longitudinal axis "k".

As depicted in FIG. 7, the first jaw member 22 may include a sensor 98 mounted to, e.g., its inner jaw surface 22i. The sensor 98 may be capable of detecting the presence of blood flow, velocity of blood flow or blood pressure within the tissue, e.g., a blood vessel, during opening and closing of the first and second jaw members 22, 24 about the blood vessel. One or more wires (not shown) may communicate with the sensor and couple with a control/monitor. Suitable sensors 98 include flow sensors, ultrasonic sensors, optical sensors or the like. [INVENTOR, FEEL FREE TO ADD A SENSOR TYPE]. The data collected by the sensor 98 may provide critical information concerning the health of the tissue.

The use of the grasping instrument 10 in grasping and clamping tissue will now be discussed. Referring initially to FIGS. 7-8, the grasping instrument 10 is depicted with the first and second jaw members 22, 24 in the approximated condition. The first and second jaw members 22, 24 are normally biased towards the approximated condition through the interaction of the spring 48 against the piston 50 which drives the inflatable membrane 52 and the drive member 54 in the proximal direction thereby also driving the carriage 40 coupled to the drive member 54 in the proximal direction. Initially, the inflatable membrane 52 may be at least partially filled with fluids or be devoid of fluids. [INVENTOR, PLEASE CONFIRM] With the carriage 40 in its initial proximal position, the jaw members 22, 24 are in the approximated condition with the internal jaw surfaces 22i, 24i contacting or in close proximity.

Figure 11:
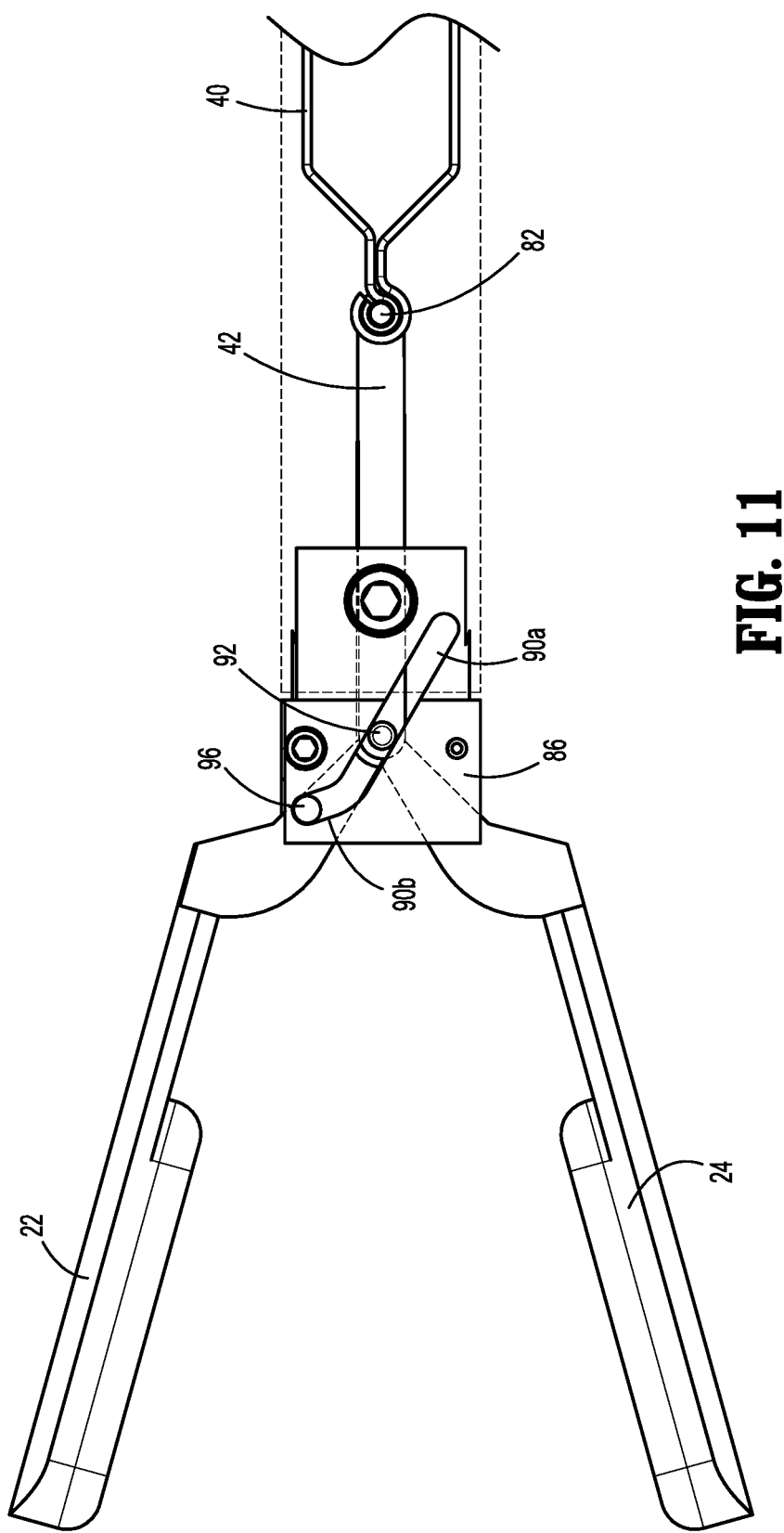
FIG. 11 is a view illustrating the first and second jaw members in the open condition.

The tissue to be grasped by the first and second jaw members 22, 24 is identified. With reference to FIGS. 9-10, the first and second jaw members 22, 24 are moved to the open condition by advancing the manually engageable knob 28 and the pusher tube 30 of the inner pusher 26 in the distal direction. During this advancing movement, the pusher tube 30 engages the proximal end 40p of the carriage 40 and advances the carriage 40 in the distal direction to an advanced distal position thereof. As best depicted in FIG. 11, upon distal movement of the carriage 40 and the links 42, the pin mounts 92 and the cam pins 96 traverse the cam slots 90 whereby the cam pins 96 enter the second slot portions 90b of the cam slots 90 causing the first and second jaw members 22, 24 to open rapidly due to the angular arrangement of the second slot portions 90b and assume the fully open condition as shown.

Figure 12:
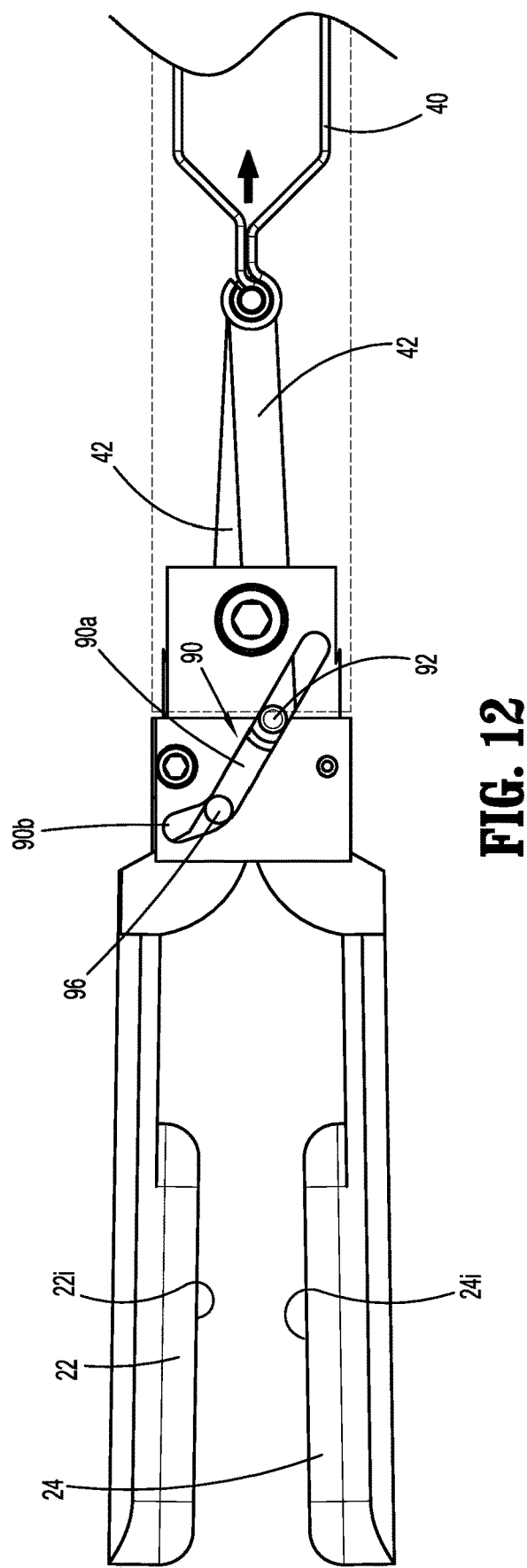
FIG. 12 is a view illustrating the first and second jaw members transitioning to a parallel relation upon movement toward the approximated condition.

While in the open condition, the first and second jaw members 22, 24 are positioned about the tissue and the manually engageable knob 28 is released thereby effecting movement of the inner pusher 26, including the pusher tube 30 and the manually engageable knob 28, to the normal proximal position under the influence of the pusher spring 34. The carriage 40 may also be released from engagement with the pusher tube 30 and moves toward its initial proximal position of FIG. 8 under the influence of spring 48 (FIG. 3). Upon proximal movement of the links 42 and the carriage 40, the cam pins 96 traverse the second slot portions 90b of the cam slots 90 of the jaw mounts 84, 86 and enter the first slot portions 90a. As discussed hereinabove and best depicted in FIG. 12, the first and second jaw members 22, 24, e.g., at least the inner jaw surfaces 22i, 24i of the first and second jaw members 22, 24, are in parallel relation upon movement toward the approximated condition through the traversing movement of the pin mounts 92 and the cam pins 96 within the first slot portions 90a of the cam slots 90. This is due to the arrangement of the first oblique angles of the first slot portions 90a as discussed hereinabove. The parallel relationship of the first and second jaw members 22, 24 enhances uniform grasping and clamping of the targeted tissue.

Figure 13:
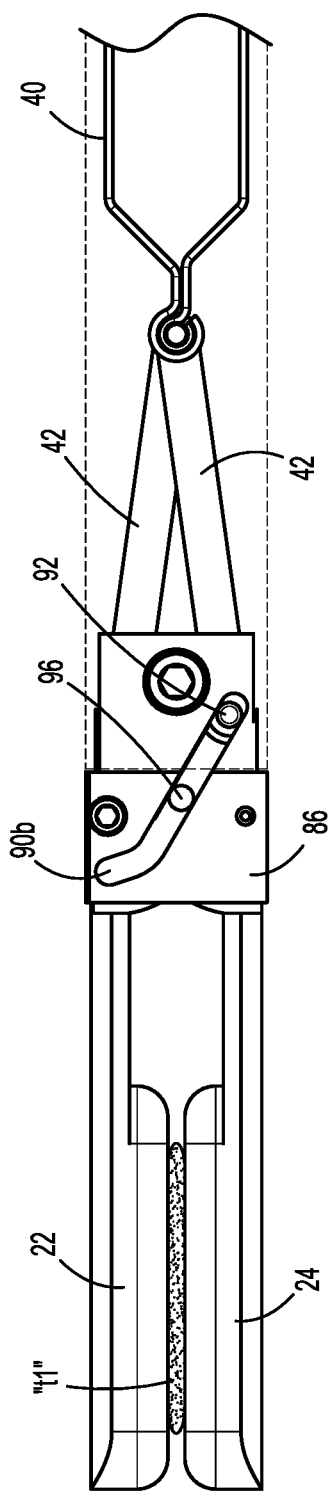
FIG. 13 is a side plan view of the first and second jaw members clamping relatively thin tissue.
Figure 14:
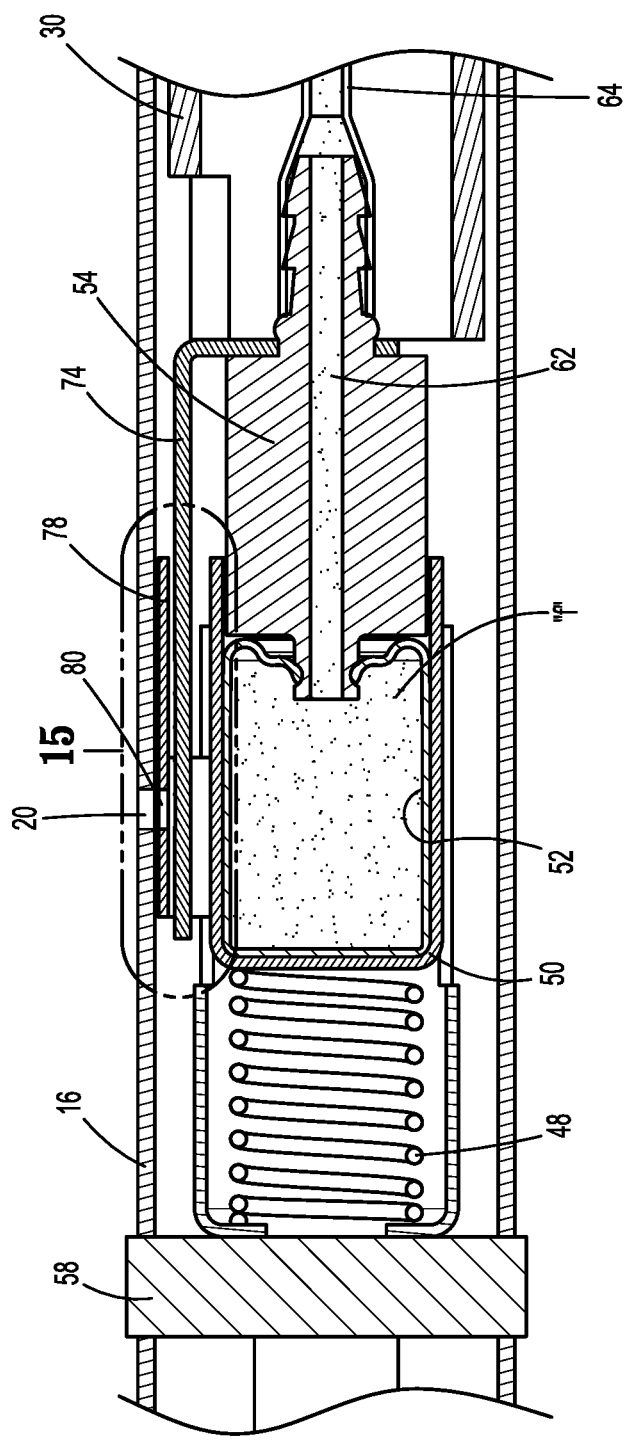
FIG. 14 is a cross-sectional view illustrating arrangement of components of the tissue measuring mechanism while the first and second jaw members clamp the relatively thin tissue.

FIGS. 13-14 illustrate the grasping instrument 10 with the first and second jaw members 22, 24 moved toward the approximated condition to grasp relatively thin tissue "t1". To obtain an accurate measurement of the thickness of the tissue "t1" disposed between the first and second jaw members 22, 24, fluids "f" are introduced through the fluid conduit 64 to pass through the flow passage 62 of the drive member 54 and enter the inflatable membrane 52 to expand the inflatable membrane 52 to a predefined internal pressure, and thereby distally advance the piston 50 against the bias of the spring 48. The predefined internal pressure may range from about 1 psi to about 3 psi. Other values are also contemplated. In embodiments, the predefined internal pressure within the inflatable membrane 52 is selected to cause compression of the spring 48 a predetermined known distance thus also permitting advancement of the piston 50 the same known distance regardless of the thickness of the tissue clamped between the first and second jaw members 22, 24. Otherwise stated, the spring 48 has a spring constant limiting movement of the piston 50 to the predetermined known distance upon inflation of the inflatable membrane 52 to the predefined internal pressure. Since this distance of travel is constant, the viewing window 80 of the bar mount 78 of the piston 50 may be selectively positioned to be in alignment with the viewing window 20 extending through the wall of the outer tube 16.

Figure 15:
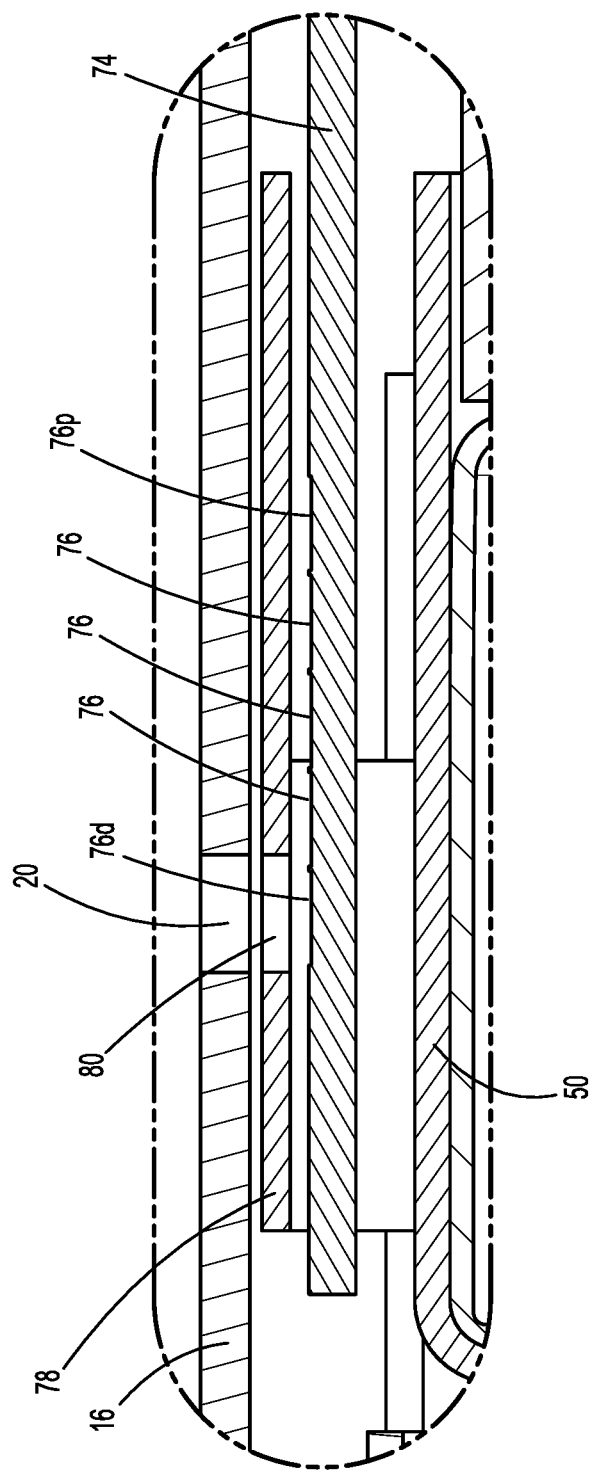
FIG. 15 is an enlarged view of the area of detail identified in FIG. 14.

Simultaneously with the expansion of the inflatable membrane 52, the drive member 54 and the carriage 40 are driven proximally to move the links 40 and the first and second jaw members 22, 24 toward the approximated condition thereby applying a clamping force on the tissue "t1" between the first and second jaw members 22, 24. In embodiments, the clamping force, which is correlated to the predefined internal pressure within the inflatable membrane 52, is selected to uniformly clamp and occlude the tissue "t1" without overly compressing the tissue "t1", i.e., the predefined internal pressure within the inflatable membrane 52 is selected to apply the desired clamping force of the first and second jaw members 22, 24 on the tissue "t1". As noted above, the predetermined distance of travel of the piston 50 is constant and selected to align the viewing window 80 of the piston 50 with the viewing window 20 of the outer tube 16. The distance of travel of the drive member 54 and the carriage 40 is limited by the thickness of the tissue subjected to the clamping force between the first and second jaw members 22, 24, i.e., the carriage 40 is displaced from its initial proximal position since the first and second jaw members 22, 24 cannot assume the approximated condition due to the presence of the tissue "t1". Thus, the indicator bar 74 of the carriage 40 is also displaced a distance corresponding to the thickness of the tissue "t1" clamped between the first and second jaw members 22, 24. This distance is represented by the visual indicator 76 which is positioned for viewing through the aligned viewing windows 20, 80 of the outer tube 16 and the piston 50, respectively. The clinician then views the visual indicator 76 of the indicator bar 74 aligned and visible through the windows 20, 80 to ascertain the thickness of the compressed tissue "t1". As noted above, the visual indicator 76 may be color-coded and/or include a numerical value which corresponds to the measured thicknesses of the clamped tissue "t1". In FIGS. 14-15, the tissue "t1" compressed between the first and second jaw members 22, 24 is relatively thin. Thus, the carriage 40 along with the indicator bar 74 is more adjacent its initial proximal position. In this position of the indicator bar 74, the distal most visual indicators 76 corresponding to relatively thin tissue would be visible through the aligned viewing windows 20, 80. In this embodiment, the distal most visual indicator 76d is visible.

Figure 16:
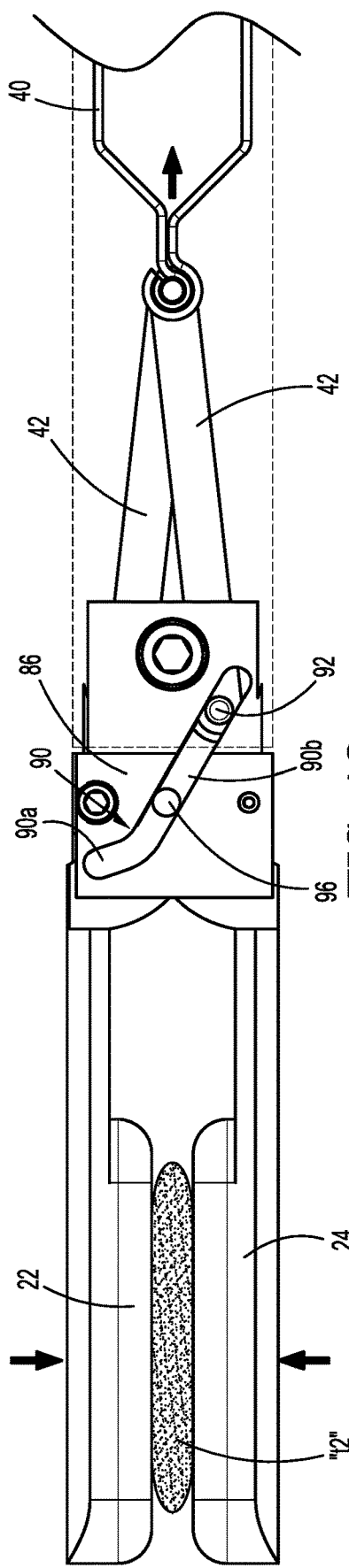
FIG. 16 is a side plan view of the first and second jaw members clamping relatively thick tissue.
Figure 17:
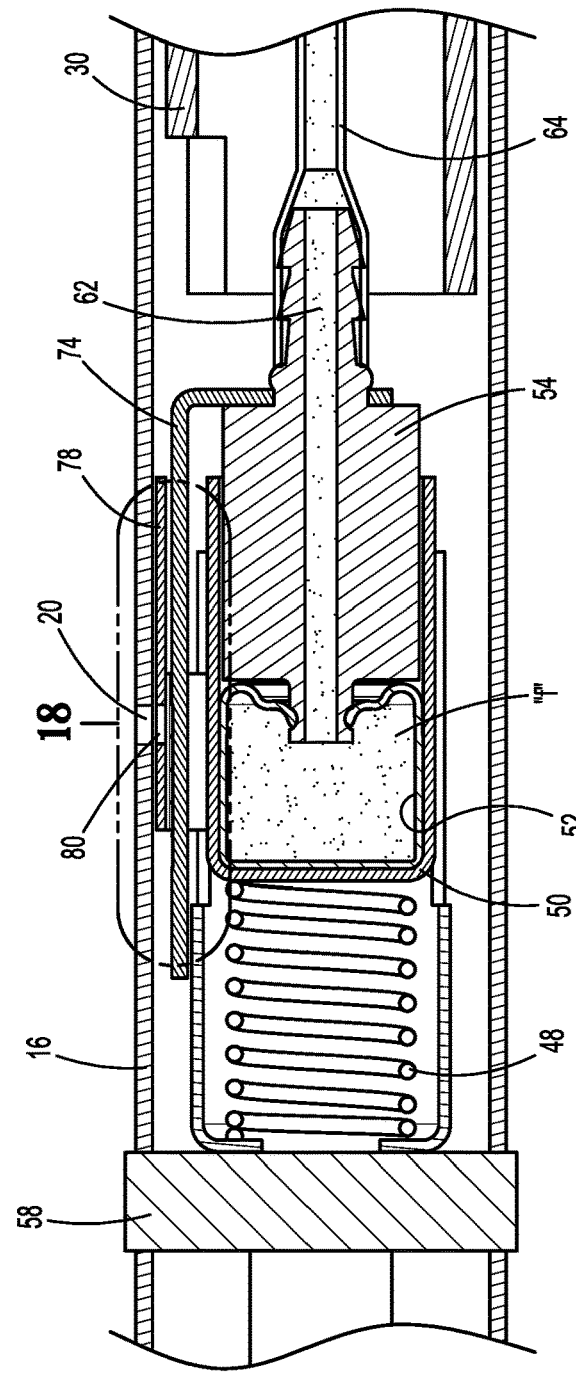
FIG. 17 is a cross-sectional view illustrating arrangement of components of the tissue measuring mechanism while the first and second jaw members clamp the relatively thick tissue.
Figure 18:
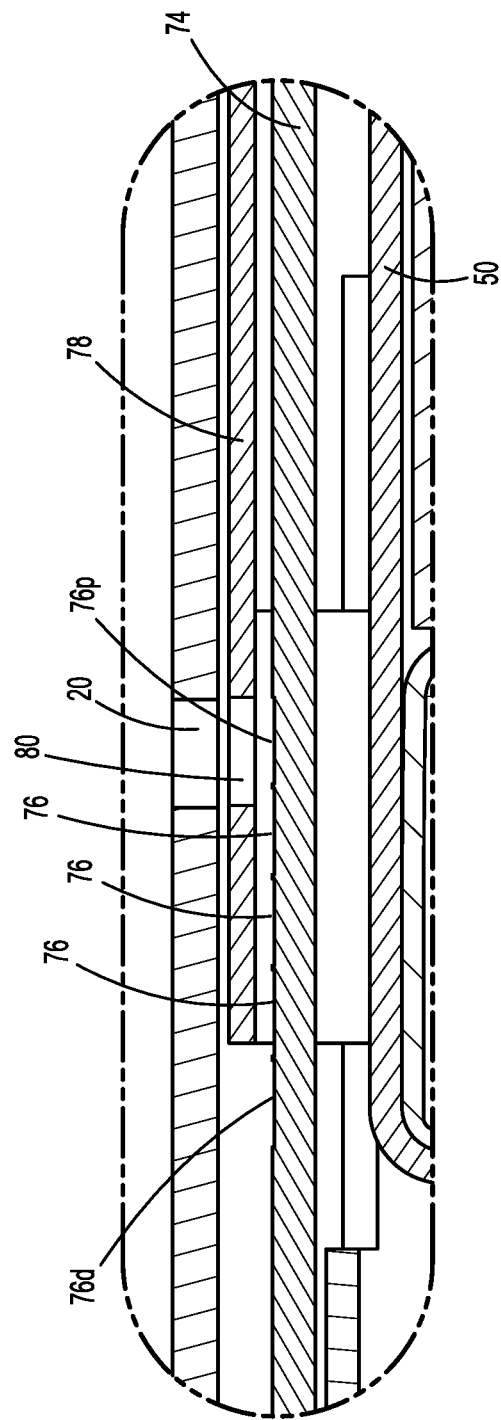
FIG. 18 is an enlarged view of the area of detail identified in FIG. 17.

FIGS. 16-18 illustrate the first and second jaw members 22, 24 grasping and clamping tissue "t" with a greater thickness. As shown, the carriage 40 is more distally positioned relative to its corresponding position for a more thin tissue. The inflatable membrane 52 is inflated to its predefined internal pressure which advances the piston 50 the same predetermined known distance to align the viewing window 80 of the piston 50 with the viewing window 20 of the outer tube 16. Simultaneously therewith, the drive member 54 and the carriage 40 are moved in the proximal direction to move the first and second jaw members 22, 24 toward the approximated condition to apply the clamping force to tissue "t2" therebetween. However, due to the presence of the relatively thick tissue "t2", the carriage 40 and thus the indicator bar 74 are more distally located thereby aligning the proximal visual indicators 76 with the viewing windows 20, 80. In this embodiment, the proximal most visual indicator 76p is aligned with, and viewable through, the viewing windows 20, 80 due to the relatively thick tissue "t2" secured between the first and second jaw members 22, 24.

Figure 19:
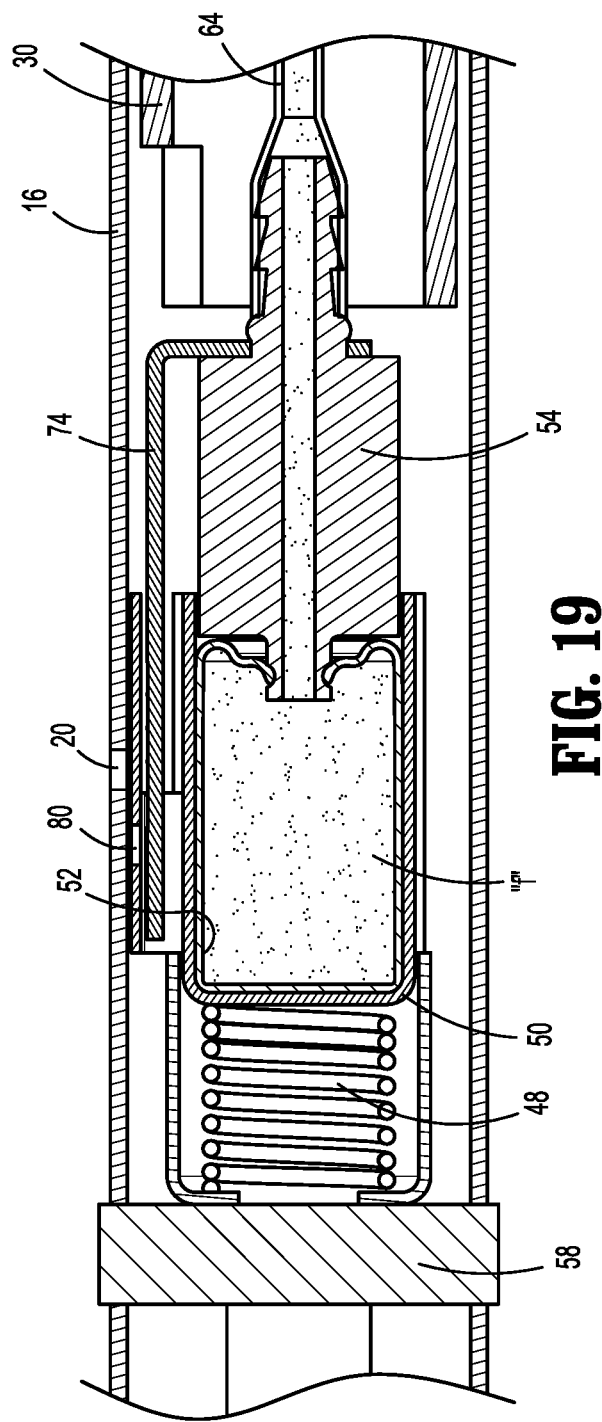
FIG. 19 is a cross-sectional illustrating arrangement of components of the tissue measuring mechanism with the first and second jaw members in an over compressed condition.

FIG. 19 illustrates the components of the measuring mechanism when the inflatable membrane 52 is over inflated, i.e., subjected to an internal pressure greater than the predefined internal pressure associated with the prior embodiments, to overly compress the tissue between the first and second jaw members 22, 24. This may be desirable to completely occlude blood flow within the compressed tissue to obtain blood flow or pressure measurement within the tissue, e.g., a blood vessel. For example, the blood vessel can be uniformly occluded through the parallel closure of the first and second jaw members 22, 24. The first and second jaw members 22, 24 may then be slowly moved toward the open condition by advancement of the inner pusher 26 in the manner discussed hereinabove. The sensor 98 within the first jaw member 22 may be utilized to detect when the blood begins to flow, the blood flow rate or the blood pressure at this location thereby providing an indication of the health of the tissue. In addition, the over inflation of the inflatable membrane 52 drives the piston 50 a greater distance against the spring 48 such that the viewing window 80 of the piston 50 is distal of the viewing window 20 of the outer tube 16. This provides confirmation to the clinician that the first and second jaw members 22, 24 are in an overly compressed condition.

From the foregoing and with reference to the various figure drawings, those skilled in the art will appreciate that certain modifications can also be made to without departing from the scope of the present disclosure. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto. No representation is made that the drawings are exactly to scale.

What is claimed is:

1. A surgical grasping instrument for clamping tissue, comprising:
    an outer tube defining a longitudinal axis and having proximal and distal ends;
    first and second jaw members supported adjacent the distal end of the outer tube, the first and second jaw members configured for movement between an open condition to receive tissue therebetween and an approximated condition to engage the tissue;
    a carriage mounted within the outer tube and operatively coupled to the first and second jaw members, the carriage configured for longitudinal movement between an initial proximal position and an advanced distal position to cause corresponding movement of the first and second jaw members between the approximated condition and the open condition;
    a piston operatively coupled to the carriage;
    an inflatable membrane disposed within the piston, the inflatable membrane selectively inflatable to a predefined internal pressure to cause corresponding distal longitudinal movement of the piston a predetermined distance and to cause proximal longitudinal movement of the carriage to apply a clamping force to the tissue disposed within the first and second jaw members; and
    an indicator bar coupled to the carriage and having visual indicators corresponding to various degrees of thickness of the tissue disposed within the first and second jaw members when subjected to the clamping force of the first and second jaw members.

2. The grasping instrument according to claim 1 wherein the first and second jaw members define internal jaw surfaces, the internal jaw surfaces being in general parallel relation during movement toward the approximated condition.

3. The grasping instrument according to claim 1 including a drive member operatively coupled to the carriage and engageable with the inflatable membrane, the drive member configured for proximal longitudinal movement upon inflation of the inflatable membrane to the predefined internal pressure to cause longitudinal movement of the carriage toward the initial proximal position.

4. The grasping instrument according to claim 3 including a spring disposed adjacent the piston.

5. The grasping instrument according to claim 4 wherein the spring includes a spring constant configured to limit distal longitudinal movement of the piston for the predetermined distance upon inflation of the inflatable membrane to the predefined internal pressure.

6. The grasping instrument according to claim 1 wherein the outer tube includes a viewing window, the viewing window permitting viewing of one of the visual indicators of the indicator bar when the tissue is subjected to the clamping force, the one of the visual indicators corresponding to a specific degree of thickness of the tissue subjected to the clamping force.

7. The grasping instrument according to claim 6 wherein the piston includes an indicator mount for at least partial reception of the indicator bar, the indicator mount including a viewing window, the viewing window positioned to be in alignment with the viewing window of the outer tube upon movement of the piston the predetermined distance to permit viewing of the one of the visual indicators of the indicator bar.

8. The grasping instrument according to claim 7 wherein the viewing window of the outer tube and the viewing window of the indicator mount are longitudinally displaced when the tissue is subjected to a force greater than the clamping force whereby the visual indicators are not viewable through the viewing windows of the outer tube and the indicator mount.

9. The grasping instrument according to claim 1 wherein the visual indicators of the indicator bar are arranged to correspond to different degrees of thickness of the tissue subjected to the clamping force, the visual indicators increasing in value from distal to proximal along the indicator bar.

10. The grasping instrument according to claim 1 wherein the visual indicators of the indicator bar include different color markings, each color marking corresponding to a selected degree of the thickness of the tissue subjected to the clamping force.

11. The grasping instrument according to claim 1 including an internal pusher at least partially disposed within the outer tube, the internal pusher configured for distal longitudinal movement to engage the carriage and move the carriage to the distal advanced position and the first and second jaw members to the open condition.

12. The grasping instrument according to claim 11 wherein the internal pusher is normally biased toward the proximal direction.

13. The grasping instrument according to claim 3 wherein the drive member defines a flow passage in fluid communication with an internal volume of the inflatable membrane to permit passage of fluids to control inflation of the inflatable membrane.

14. The grasping instrument according to claim 4 including an internal spring housing secured within the outer tube, the internal spring housing at least partially accommodating the spring, the piston and the inflatable membrane.

15. A surgical grasping instrument for clamping tissue, comprising:
an outer tube defining a longitudinal axis and having proximal and distal ends;
first and second jaw members supported adjacent the distal end of the outer tube, the first and second jaw members configured for movement between an open condition to receive tissue therebetween and an approximated condition to engage the tissue, internal jaw surfaces of the first and second jaw members being in general parallel relation upon movement toward the approximated condition;
a carriage mounted within the outer tube and operatively coupled to the first and second jaw members, the carriage configured for longitudinal movement between an initial proximal position and an advanced distal position to cause corresponding movement of the first and second jaw members between the approximated condition and the open condition;
a drive member coupled to the carriage;
a piston at least partially accommodating the drive member;
an inflatable membrane disposed within the piston adjacent the drive member, the inflatable membrane selectively inflatable to a predefined internal pressure to cause corresponding distal longitudinal movement of the piston a predetermined distance and to cause proximal longitudinal movement of the drive member and the carriage to apply a clamping force to the tissue disposed within the first and second jaw members;
an indicator bar coupled to the carriage and having visual indicators corresponding to various degrees of thickness of the tissue disposed within the first and second jaw members when subjected to the clamping force of the first and second jaw members; and
an internal pusher at least partially disposed within the outer tube, the internal pusher configured for distal longitudinal movement to engage the carriage and move the carriage to the distal advanced position and the first and second jaw members to the open condition.

16. The grasping instrument according to claim 15 wherein the visual indicators of the indicator bar include longitudinal markings, respective markings corresponding to the thickness of the tissue subjected to the clamping force.

* * * * *